United States Patent [19]

Hesoun et al.

[11] 4,384,118
[45] May 17, 1983

[54] 4-(3-IODOPROPARGYLOXY) PYRIMIDINE DERIVATIVES

[75] Inventors: Dusan Hesoun; Bohumir Vondracek, both of Usti n/Labem; Jana Turinova, Prague, all of Czechoslovakia

[73] Assignee: SPOFA, spojene podniky pro zdravotnickou vyrobu, Prague, Czechoslovakia

[21] Appl. No.: 273,444

[22] Filed: Jun. 15, 1981

[30] Foreign Application Priority Data

Jun. 13, 1980 [CS] Czechoslovakia ............... 4192-80

[51] Int. Cl.³ .................. C07D 239/47; C07D 239/56
[52] U.S. Cl. .................................... 544/309; 544/319; 544/320
[58] Field of Search ................. 544/319, 320, 309

[56] References Cited

U.S. PATENT DOCUMENTS 3,907,797 9/1975 Budesinsky et al. ............... 544/298
3,980,781 9/1976 Snell et al. ......................... 544/320

Primary Examiner—Paul M. Coughlan, Jr.

[57] ABSTRACT 4-(3-Iodopropargyloxy) pyrimidine derivatives of the general formula

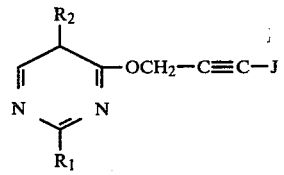

wherein $R_1$ is selected from among a halogen atom, an amino group, a $C_1$–$C_4$ alkylamino or a $C_1$–$C_4$ alkylthio group, and $R_2$ is selected from among a hydrogen atom, a halogen atom, a $C_1$–$C_4$ alkyl group or a $C_1$–$C_4$ alkoxy group, are disclosed. The described compounds are prepared by reacting a 4-halopyrimidine with propargyl alcohol and iodinating the resultant product in the 3 position of the propargyl chain.

4 Claims, No Drawings

4-(3-IODOPROPARGYLOXY) PYRIMIDINE DERIVATIVES

This invention relates to pyrimidine derivatives and to a process for the preparation thereof. More particularly, the present invention relates to 4-(3-iodopropargyloxy) pyrimidine derivatives which evidence antimycotic and antibacterial activity and to the preparation thereof.

The pyrimidine derivatives of the present invention are of the general formula

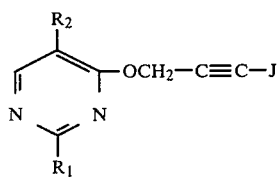
(1)

wherein $R_1$ is selected from among a halogen atom, an amino, a $C_1$–$C_4$ alkylamino group and a $C_1$–$C_4$ alkylthio group, and $R_2$ is selected from among a hydrogen atom, a halogen atom, a $C_1$–$C_4$ alkyl group and a $C_1$–$C_4$ alkoxy group.

Heretofore, the 5-(3-iodopropargyloxy) pyrimidine derivatives were reported in the literature (Czechoslovakian author certificate No. 158,984), such derivatives also evidencing antimycotic and antibacterial activity. However, these prior art derivatives evidenced such activity to a limited degree. The compounds of the present invention differ markedly from such prior art derivatives with respect to both antimycotic and antibacterial activity. Thus, for example, minimum inhibitory concentrations of 2-methylthio-4-(3-iodopropargyloxy) pyrimidine, 2-methylthio-5-methoxy-4-(3-iodopropargyloxy) pyrimidine and 2-amino-5-methoxy-4-(3-iodopropargyloxy) pyrimidine is Aspergillus niger are 0.3 to 0.7 μg/ml. The activity of these compounds against Trichophyton mentagrophytes also lies in the same range, such activity being comparable with that of the best antimycotic agents previously known. The activity of other compounds of the above-identified formula (1) against Aspergillus niger is even higher, i.e., an order of magnitude higher than the noted iopropargyloxy pyrimidine derivatives. For example, the minimum inhibitory concentration of 2-methylthio-5-ethoxy-4-(3-iodopropargyloxy) pyrimidine, 2-ethylthio-5-methoxy-4-(3-iodopropargyloxy) pyrimidine and 2-methylthio-5-bromo-4-(3-iodopropargyloxy) pyrimidine is 0.07, 0.03 and 0.01 μg/ml, respectively.

For comparative purposes, three of the compounds of formula (1) were compared with Clotrimazole and Haloprogine, well known prior art antimycotic compounds. Comparisons of minimum inhibitory concentration in μg/ml. were made with respect to four strains of bacteria. The data recorded are tabulated in Table A below.

TABLE A

| | Minimum Inhibitory Concentrations, μg/ml | | | |
|---|---|---|---|---|
| | SP | TM | CA | AN |
| Compound I | 0.3 | 0.07 | 3.1 | 0.01 |
| Compound II | 0.15 | 0.07 | 0.7 | 0.3 |
| Compound II | 0.3 | 0.3 | 3.1 | 0.03 |
| Clotrimazole | 3.1 | 0.03 | 0.3 | 3.1 |

TABLE A-continued

| | Minimum Inhibitory Concentrations, μg/ml | | | |
|---|---|---|---|---|
| | SP | TM | CA | AN |
| Haloprogine | | 0.6 | 1.2 | |

Key
SP = Sacharomyces Pastorianus
TM = Trichophyton Mentagrophytes
CA = Candida Alicans
AN = Aspergillus Niger
Compound I = 2 propylthio-5-methoxy-4-(3 iodoprogargyloxy) pyrimidine
Compound II = 2-allylthio-4-(3-iodopropargyloxy) pyrimidine
Compound III = 2-allylthio-5-methoxy-4-(3-iodopropargyloxy) primidine Additionally, certain compounds of the invention were evaluated with respect to other mold species. Thus, for example, 2-ethylthio-4-(3 iodopropargyloxy) pyrimidine was evaluated with respect to the species identified in Table B, below and the noted minimum inhibitory cencentrations determined:

TABLE B

| Mold Species | Minimum Inhibitory Concentration μg/ml |
|---|---|
| Microsporum gypseum | 0.3 |
| Microsporum Canis | 0.15 |
| Epidermophyton floccosum | 0.3 |
| Trichophyton verrucosum | 0.15 |
| Keratinomyces ajelloi | 0.3 |
| Trichophyton rubrum | 0.07 |
| Sporotrichum cejpii | 0.3 |
| Trichophyton schoenleinii | 0.03 |

The compounds described herein are particularly advantageous in that their ease of preparation facilitates economical large-scale production. Thus, the novel compounds may be obtained by reacting 4-halopyrimidines of the general formula

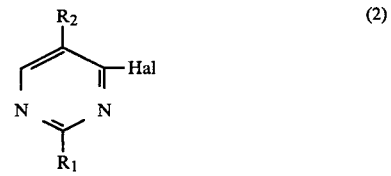
(2)

wherein $R_1$ and $R_2$ are as defined in formula (1) and Hal is a halogen atom, with propargyl alcohol, and, subsequently, subjecting the propargyl chain of the resultant intermediary product in position number 3 to iodination. This reaction is conveniently conducted in the presence of an inert organic solvent in the presence of an agent which binds the resultant hydrogen halide at the boiling temperature of the reaction mixture. Solvents suitable for this purpose include benzene, toluene, dioxane and acetonitrile whereas acceptable binding agents may be selected from among an alkali metal amide, hydroxide or carbonate. The addition of a phase transfer catalyst such as triethyl benzyl ammonium chloride enhances the reaction when a mixture of benzene and toluene are employed as the inert organic solvent with an aqueous alkali solution.

The iodination of the resultant 4-propargyloxy pyrimidines may conveniently be effected either with elemental iodine or with an alkali metal iodide. When utilizing the alkali metal iodide an oxidizing agent such as sodium hypochlorite is employed in a $C_1$–$C_3$ alkanol medium and in the presence of an aqueous alkali metal hydroxide solution.

The invention will be more readily understood by reference to the following detailed examples. It will be understood by those skilled in the art that these examples are solely for the purpose of exposition and are not to be construed as limiting.

EXAMPLE 1

3 grams of 2-methylthio-4-chloro pyrimidine in 30 ml of benzene was reacted with 3 ml of an aqueous 40% sodium hydroxide solution, 0.3 grams of triethyl benzyl ammonium chloride and 2 ml of propargyl alcohol. The resultant reaction mixture was refluxed with stirring for a period of 4 hours. Following, the mixture was cooled and 20 milliliters of water added, so resulting in separation of the benzene layer. Then, the solvent was evaporated under reduced pressure to yield 4.1 grams of 2-methylthio-4-propargyloxy pyrimidine melting at a temperature within the range of 70°–71° C. in ethanol.

EXAMPLE 2

A solution comprising 3 grams of 2-methylthio-4-chloro-5 ethoxy pyrimidine in 30 milliliters of benzene was treated with 1 gram of sodium amide and 1.5 ml of propargyl alcohol. The reaction mixture was refluxed with stirring for 5 hours. Upon cooling, the unreacted sodium amide was decomposed with water, the benzene layer separated and the solvent evaporated under reduced pressure. Crystallization of the residue from ethanol yielded 2.8 grams of 2-methylthio-4-propargyloxy-5-ethoxy pyrimidine having a melting point ranging from 84°–85° C.

EXAMPLE 3

A solution comprising 1.1 grams of 2-amino-4-chloro-5-methoxy pyrimidine in 30 milliliters of benzene was treated with 0.2 grams of triethyl benzyl ammonium chloride, 2 milliliters of an aqueous 40% sodium hydroxide solution and 1 milliliter of propargyl alcohol. The reaction mixture was refluxed with stirring for 3 hours and processed in accordance with the procedure of example 1. On crystallization from ethanol, 1 gram of 2-amino-4-propargyloxy-5-methoxy pyrimidine having a melting point within the range of 97°–99° C.

EXAMPLE 4

The procedure of example 1 was repeated utilizing 2.4 grams of 2-methylthio-4-chloro-5-bromo pyrimidine rather than the 4-chloro pyrimidine. The yield was 2 grams of 2-methylthio-4-propargyloxy-5-bromo pyrimidine having a melting point ranging from 70°–71.5° C.

EXAMPLE 5

A solution comprising 3 grams of 2-methylthio-4-propargyloxy pyrimidine in 50 milliliters of methanol was treated with a solution of 2 grams of sodium hydroxide in 20 milliliters of water and 5 grams of iodine. The reaction mixture was stirred for 2 hours at 40° C. Upon cooling to a temperature of 10° C., a product precipitated and was filtered off to yield 4.6 grams of 2-methylthio-4-(3-iodopropargyloxy) pyrimidine having a melting point ranging from 150°–152° C. in ethanol.

EXAMPLE 6

The procedure of example 5 was repeated utilizing 2-methylthio-4-propargyloxy-5-ethoxy pyrimidine. There resulted 1.2 grams of 2-methylthio-4-(3-iodopropargyloxy)-5-ethoxy pyrimidine having a melting point ranging from 132°–135° C.

EXAMPLE 7

0.5 gram of 2-amino-4-propargyloxy-5-methoxy pyrimidine was disolved in 20 ml. of ethanol and a solution comprising 0.4 gram of sodium hydroxide in 4 ml. of water added thereto. Following, 0.4 gram of sodium hypochlorite and 0.85 gram of potassium iodide were added. The resultant mixture was stirred at ambient temperature for 2 hours and cooled to 5° C. Then, the precipitated product was filtered off and washed with methanol. 0.6 grams of 2 amino-4-(3-iodopropargyloxy)-5-methoxy pyrimidine was attained having a melting point ranging from 150°–153° C.

EXAMPLE 8

A solution comprising 2.2 grams of 2-butylthio-4-propargyloxy-5-methoxy pyrimidine in 60 ml. of methanol was treated with a solution comprising 1.6 grams of sodium hydroxide in 16 ml. of water to which 3.4 grams of iodine were added. The reaction mixture was stirred for 3 hours at ambient temperature, diluted with 60 ml. of water and stirring continued for another half hour. The resultant precipitate was filtered off and crystallized from ethanol to yield 2-butylthio-4-(3-iodopropargyloxy)-5-methoxy pyrimidine having a melting point ranging from 101 to 102.5° C.

EXAMPLE 9

1 gram of 2-allylthio-4-propargyloxy pyrimidine was dissolved in 50 ml. of methanol and treated with 10 ml. of an aqueous 10% sodium hydroxide solution and 1.7 grams of iodine. After 3 hours of stirring, the precipitated product was filtered off. Upon crystallization from ethanol there resulted 0.8 gram of 2-allylthio-4-(3-isopropargyloxy) pyrimidine having a melting point ranging from 112°–114.5° C.

EXAMPLE 10

1 gram of 2 methylthio-4-propargyloxy-5-butyloxy pyrimidine was dissolved in 50 ml. of methanol and treated with 20 ml. of a 10% aqueous sodium hydroxide solution and 1.7 grams of iodine. The reaction mixture was stirred for 3 hours at 35° C., diluted with 50 ml. of water and stirring contained for another 0.5 hour. The resultant precipitate was filtered off and crystallized from ethanol to yield 1.2 grams of 2-methylthio-4-(3-iodopropargyloxy)5-butyloxy pyrimidine having a melting point ranging from 98°–103° C.

EXAMPLE 11

The procedure of example 10 was repeated utilizing 1 gram 2-methylthio-4-propargyloxy-5-bromo pyrimidine to yield 1.1 grams of 2-methylthio-4-(3 iodopropargyloxy)-5-bromo pyrimidine having a melting point ranging from 136°–138° C.

We claim:
1. 2-Amino-4-(3 iodopropargyloxy)-5-methoxy pyrimidine.
2. 2-Butylthio-4-(3-iodopropargyloxy)-5-methoxy pyrimidine.
3. 2-Allylthio-4-(3-iodopropargyloxy) pyrimidine.
4. 2-Methylthio-4-(3-iodopropargyloxy)-5-methoxy pyrimidine.